United States Patent [19]

Brown et al.

[11] Patent Number: 5,702,400
[45] Date of Patent: Dec. 30, 1997

[54] INTRAOCULAR LENS FOLDER

[75] Inventors: Kyle Brown, Fort Worth; Stephen J. Van Noy, Arlington; Yi-Ren Woo, Flower Mound; Lars D. Jensen, Arlington, all of Tex.

[73] Assignee: Alcon Laboratories, Inc., Fort Worth, Tex.

[21] Appl. No.: 766,539

[22] Filed: Dec. 11, 1996

[51] Int. Cl.[6] ........................... A61F 9/00
[52] U.S. Cl. ........................... 606/107; 623/6
[58] Field of Search ............... 606/107; 623/6; 604/165, 163

[56] References Cited

U.S. PATENT DOCUMENTS

| | | |
|---|---|---|
| D. 349,342 | 8/1994 | Van Noy et al. . |
| 4,573,998 | 3/1986 | Mazzocco . |
| 4,619,657 | 10/1986 | Keates et al. . |
| 4,834,750 | 5/1989 | Gupta . |
| 4,919,130 | 4/1990 | Stoy et al. . |
| 4,976,716 | 12/1990 | Cumming ............... 606/107 |
| 5,100,410 | 3/1992 | Dulebohn . |
| 5,139,501 | 8/1992 | Klass . |
| 5,281,227 | 1/1994 | Sussman ............... 606/107 |
| 5,290,293 | 3/1994 | Van Noy et al. . |
| 5,290,892 | 3/1994 | Namadaran et al. . |
| 5,403,901 | 4/1995 | Namadaran et al. . |
| 5,441,045 | 8/1995 | Federman et al. ............... 606/107 |
| 5,454,818 | 10/1995 | Hambleton et al. . |
| 5,613,953 | 3/1997 | Pohndorf ............... 604/165 |

*Primary Examiner*—Robert A. Hafer
*Assistant Examiner*—Justine R. Yu
*Attorney, Agent, or Firm*—Jeffrey S. Schira

[57] ABSTRACT

A single piece intraocular lens folder that has a generally planar, open frame in the shape of a rounded "A" with a rimmed, open head at the top of the "A". The base of the "A" forms a pairs of opposing legs or handles that join to form a hinge at the intersection where the handles attach to the head. The hinge allows the handle to be squeezed together and spring apart when released. Squeezing the handles together causes the sides of the head to spread apart, thereby stretching the top edge of the head rim and pulling the top edge downward toward the hinge. The open head contains a pair of support jaws and a pair of serpentine folding jaws. The location of the serpentine jaws is such that when the top edge of the head rim moves toward the hinge, the serpentine jaws are squeezed together, causing the IOL to be folded in half. The serpentine shape of the folding jaws allow the haptics to pivot downward, thereby permitting the IOL to be folded along a plurality of axes.

8 Claims, 6 Drawing Sheets

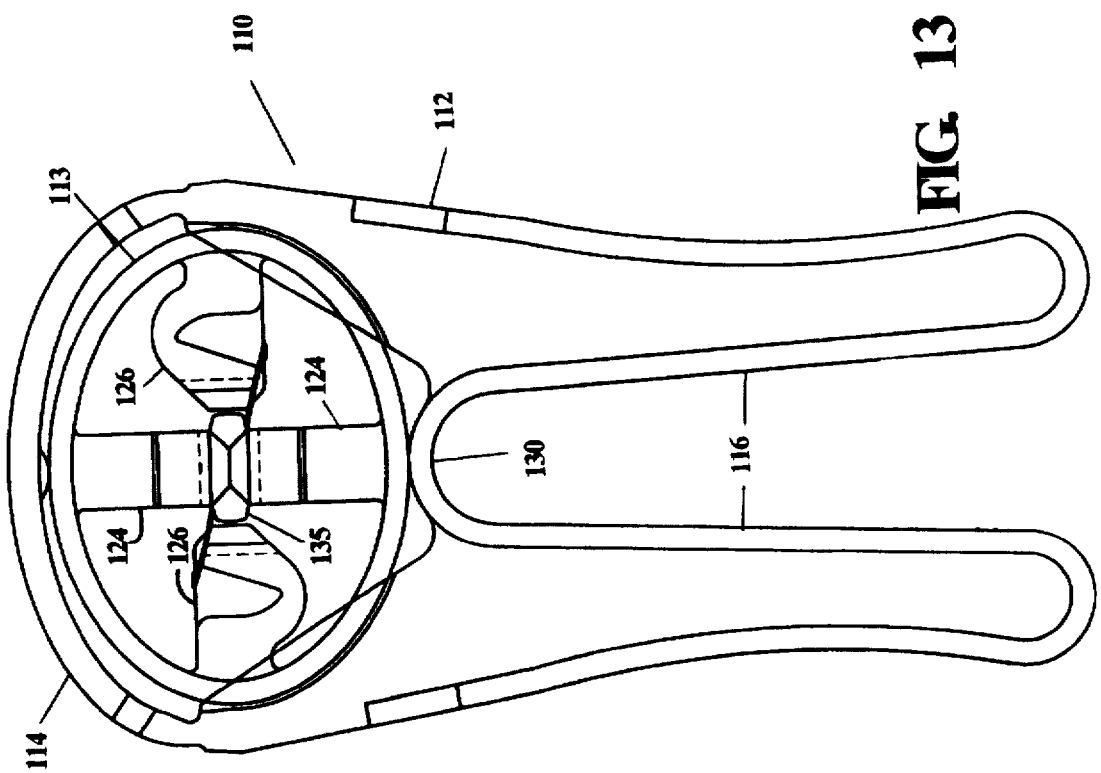
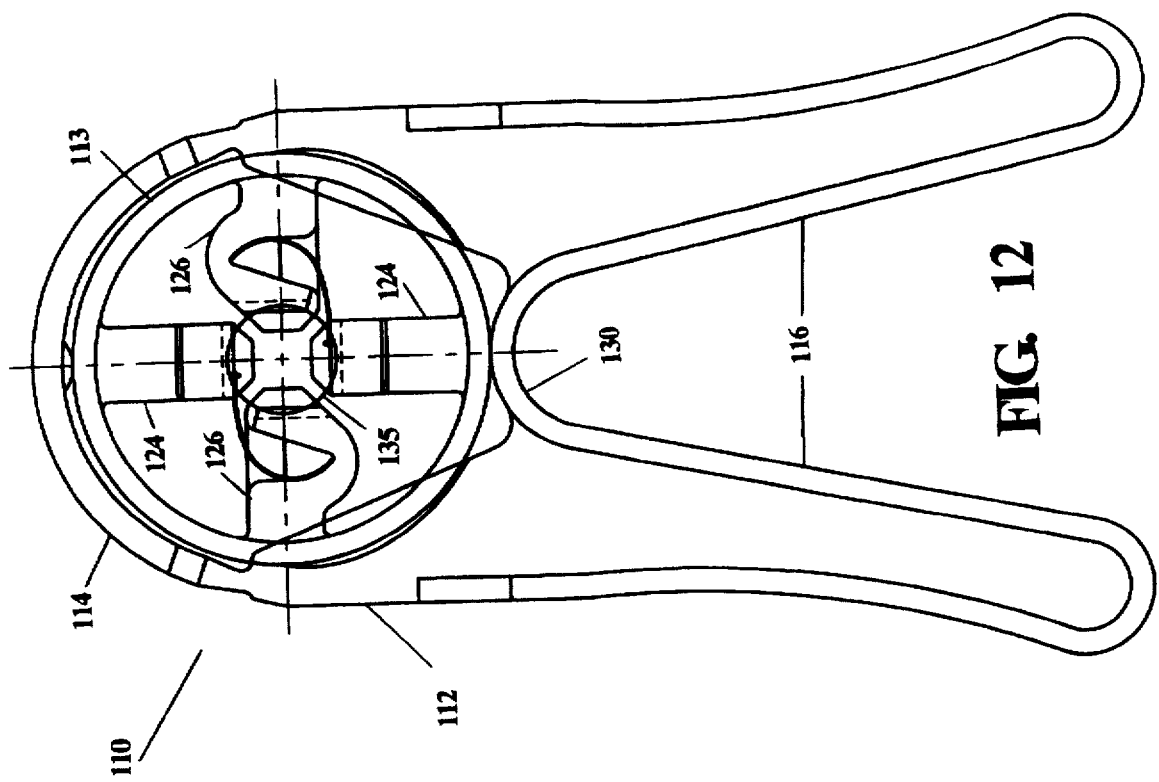

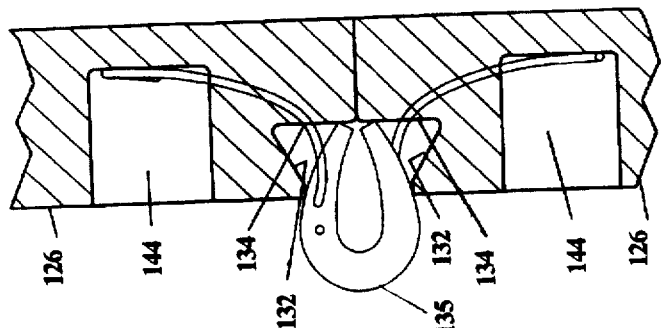
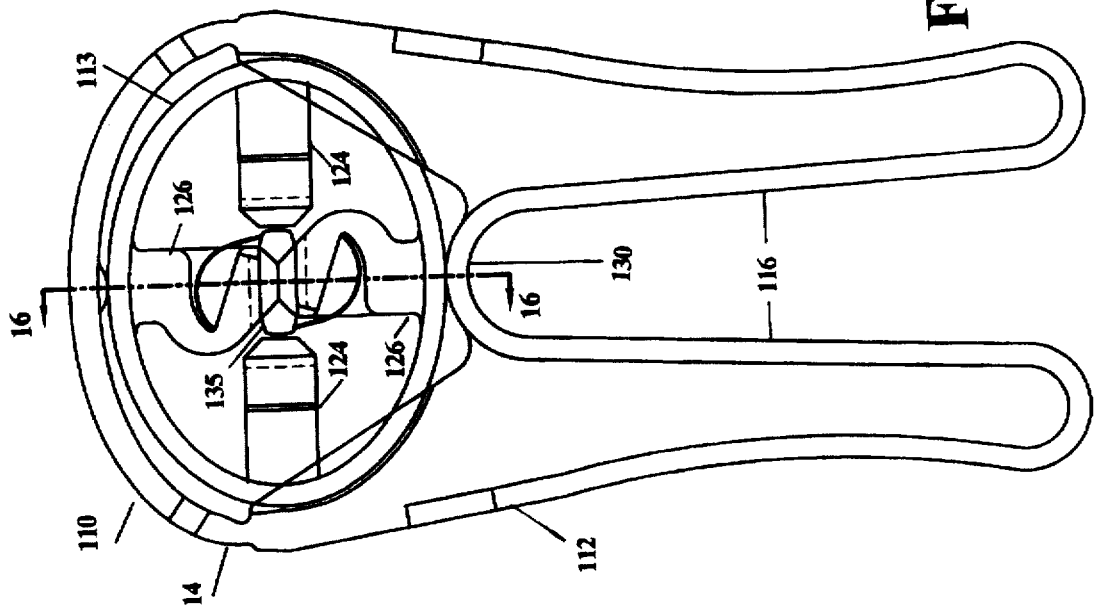
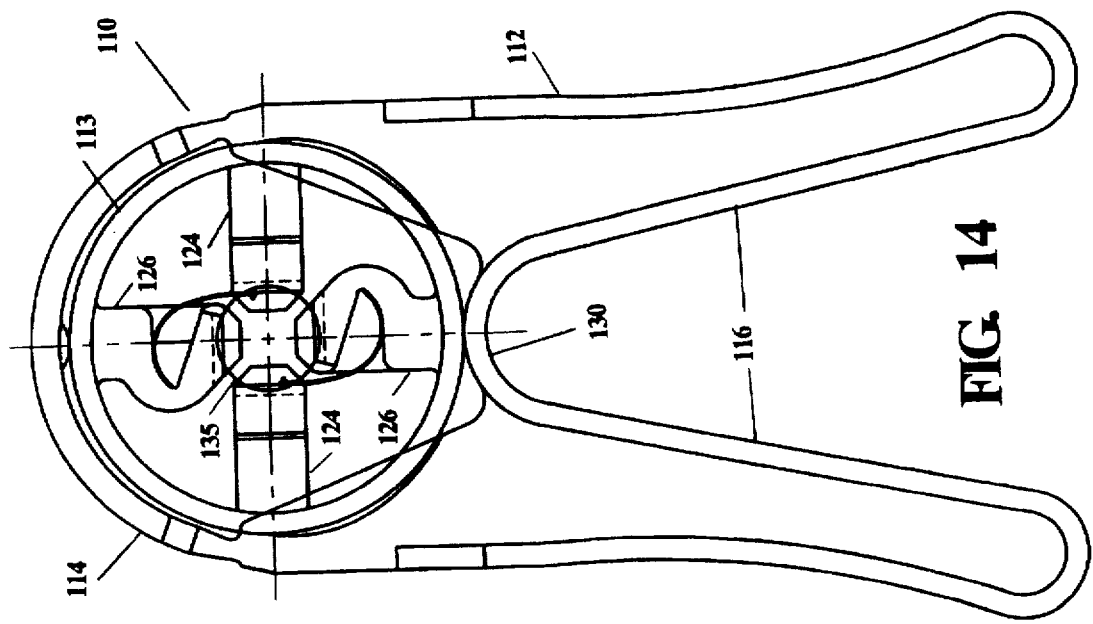

INTRAOCULAR LENS FOLDER

BACKGROUND OF THE INVENTION

The present invention relates to intraocular lenses and more particularly to foldable intraocular lenses.

For many years, the predominant method of treating a diseased lens is to remove the lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Both surgical procedures require that the anterior lens capsule be cut to allow access to the lens itself and to allow the implantation of the replacement lens, and because the capsule bag is used to hold or retain the IOL in place after surgery, the opening should be as small as possible. Although extracapsular cataract extraction has been the preferred surgical technique, phacoemulsification is becoming increasingly popular, in part because of the relatively small (around 2–3 millimeters) tunnel incision that is used with phacoemulsification.

A typical IOL comprises an artificial lens ("optic") and at least one support member ("haptic") for positioning the IOL within the capsular bag. The diameter of the optic varies depending on the design of the IOL, but an optic diameter of around 5 millimeters (mm) to 6 mm is most common. When the surgical technique used is extracapsular cataract extraction, inserting the IOL through the relatively large incision presents no particular difficulties. However, when the surgical procedure used in phacoemulsification, the surgeon typically must widen the initial 2–3 mm tunnel incision enough to allow the IOL to be inserted into the capsular bag. Enlarging the incision reduces one of the advantages of phacoemulsification because of the possibility for postoperative complications associated with large incision ocular surgery, including induced astigmatism. Therefore, rollable or foldable IOL's have been developed that can be inserted into the capsular bag with minimal widening of the phacoemulsification incision.

As discussed in U.S. Pat. Nos. 4,573,998; 4,619,657; 4,834,750; and 4,919,130, the entire contents of which is incorporated herein in its entirety by reference, foldable IOL's generally are made from polyurethane elastomers, silicone elastomers, hydrogel polymer, collagen compounds, or organic or synthetic gel compounds. The lens is rolled, compressed or crushed by a special syringe or forceps and placed into the capsular bag without enlarging the incision. While these IOL's and insertion devices work well, the insertion devices are bulky and require practice to master their use.

A second generation of foldable IOL's have recently been introduced that are made from monomers derived from acrylacrylate or methacrylates and a crosslinking agent. Such monomers are described more fully in commonly assigned U.S. Pat. Nos. 5,290,892 and 5,403,901, the entire contents of which is incorporated by reference. Such materials are advantageous because they have higher refractive indices and, hence, allow the IOL to be thinner.

Prior to the present invention, to implant IOL's made from such acrylic materials, a special duckbill forceps with rounded jaws that will not close together completely (so as not to press the sides of the folded IOL together) was used. However, theses forceps cannot, by themselves, fold the IOL, and the surgeon must hold the IOL with a second needle-nose or tying forceps while enveloping and folding the IOL with the duckbill forceps. This technique, while reliable, requires the use of two hands and a great deal of practice to master.

One IOL folder disclosed in U.S. Pat. No. 5,100,410 uses a pair of opposing jaws that when pressed together folds the IOL within a pair of duckbill forceps. However, the recessed jaws of the folder disclosed in this patent requires that the forceps be held in place on either side of the lens during folding operation, making it difficult for one persons (such as the nurse) to fold the IOL while another person (such as the surgeon) holds the forceps.

Another IOL folder disclosed in U.S. Pat. No. 5,139,501 uses a base with a fixed jaw and an opposing, movable jaw. The IOL is placed between the jaws and the movable jaw is pressed toward the fixed jaw, thereby folding the soft IOL. However, this folder must be assembled from several pieces, increasing its manufacturing cost.

One folder suitable for use with soft IOLs is disclosed in U.S. Pat. No. 5,454,818, the entire contents of which is incorporated herein by reference. The folding jaws of this folder, however, allow the IOL to be folded in only one direction, along the longitudinal axis in line with the haptics (12 o'clock to 6 o'clock). Many surgeons prefer that the IOL be folded along the transverse axis (9 o'clock to 3 o'clock), so that the opposing haptics are brought into contact.

Accordingly, a need continues to exist for an inexpensive, one-handed device that will fold easily a soft IOL that will allow the IOL to be folder along a plurality of axes.

BRIEF DESCRIPTION OF THE INVENTION

The present invention improves upon prior art IOL folders by providing a plastic, single piece folder that easily and reliably folds an IOL. The device has a generally planar, open flame in the shape of a rounded "A" with a rimmed, open head at the top of the "A". The base of the "A" forms a pair of opposing legs or handles that join to form a hinge at the intersection where the handles attach to the head. The hinge allows the handle to be squeezed together and spring apart when released. Squeezing the handles together causes the sides of the head to spread apart, thereby stretching the top edge of the head rim and pulling the top edge downward toward the hinge. The open head contains a pair of support jaws and a pair of folding jaws, the folding jaws being serpentine in shape. The location of the serpentine jaws is such that when the top edge of the head rim moves toward the hinge, the serpentine jaws are squeezed together, causing the IOL to be folded in half. The serpentine shape of the jaws allow the haptics to pivot downward, thereby permitting the IOL to be folded along a plurality of axes.

Accordingly, one objective of the present invention is to provide a device for folding intraocular lenses.

Another objective of the present invention is to provide an intraocular lens folder that is easy to use.

Still another objective of the present invention is to provide a single piece intraocular lens folder.

Yet another objective of the present invention is to provide an intraocular lens folder that permits folding of the lenses along a plurality of axes.

These and other objectives and advantages of the present invention will become apparent from the detailed description and claims which follow.

BRIEF DESCRIPTION OF THE DRAWINGS

FIG. 12 is a plan view of the second embodiment of the present invention illustrating the support jaws aligned horizontally and the intraocular lens in an unfolded condition.

FIG. 13 is a plan view of the second embodiment of the present invention similar to FIG. 12, but showing the intraocular lens in a folded condition.

FIG. 14 is a plan view of the second embodiment of the present invention illustrating the support jaws aligned vertically and the intraocular lens in an unfolded condition.

FIG. 15 is a plan view of the second embodiment of the present invention similar to FIG. 14, but showing the intraocular lens in a folded condition.

FIG. 16 is a is a cross-sectional view of the serpentine support jaw of the second embodiment of the present invention taken along line 16—16 in FIG. 15 and showing the intraocular lens in a folded condition.

DETAILED DESCRIPTION OF THE INVENTION

Figure 2:
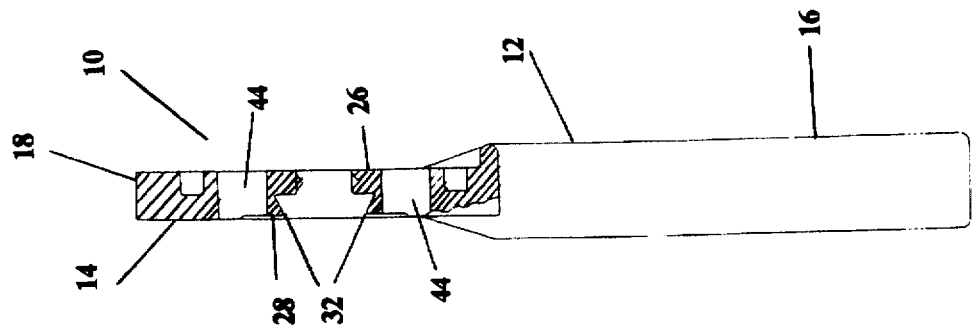
FIG. 2 is a cross-sectional view of the present invention taken along line 2—2 in FIG. 1.

As seen in FIGS. 1, 3, 5 and 6, intraocular lens folder 10 of the present invention generally comprises frame 12 having a head 14 and handles 16. Frame 12 is preferably molded in one piece from a relatively soft plastic such as polypropylene or polyethylene. Head 14 generally is defined by a deformable, arcuate rim 18 and upper portions 20 so as to give head 14 a half ring-like appearance in plan view, as can best be seen in FIGS. 1 and 3. Projecting into hollow center 22 of head 14 are a plurality of opposing jaws 24, 26 and 28, jaw 28 being integrally formed in rim 18, jaw 26 being opposite jaw 28 and integrally formed in hinge 30 between handles 16 and support jaws 24 being opposing and integrally formed in portion 20 of handles 16.

As best seen in FIGS. 1, 3, 6, 7 and 8 folding jaws 26 and 28 are generally serpentine in shape, contain clamping faces 32 that are undercut or relieved and contain a sill 34, thereby providing a stable platform for positioning the IOL (not shown) and ensuring that the IOL will consistently fold in the correct direction. The serpentine shape of jaws 26 and 28 forms passages 44, useful in the manner described below. Clamping faces 32 may also contain one or more pins 38 on either jaw 26 or jaw 28 that fit into mating hole(s) 40 on the opposite jaw when jaw 28 is forced into contact with jaw 26 as hereinafter described. Pin 38 and hole 40 ensure that jaws 26 and 28 remained aligned during contact. Jaws 24, 26 and 28 may also contain holes 52 that fit over pins (not shown) in an outer shipping container (not shown) and prevent folder 10 from moving within the shipping container. Support jaws 24 may include a recess 42 into which the haptics (not shown) of the IOL are placed to help hold the IOL in place during storage, shipping and folding.

Figure 1:
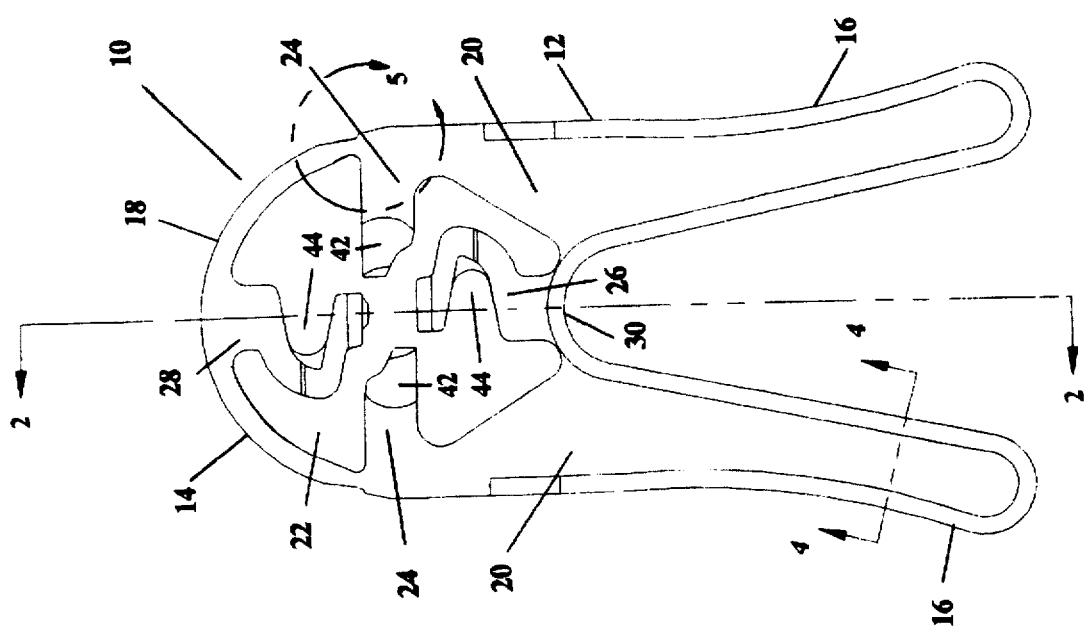
FIG. 1 is a top plan view of the intraocular lens folder of the present invention.
Figure 5:
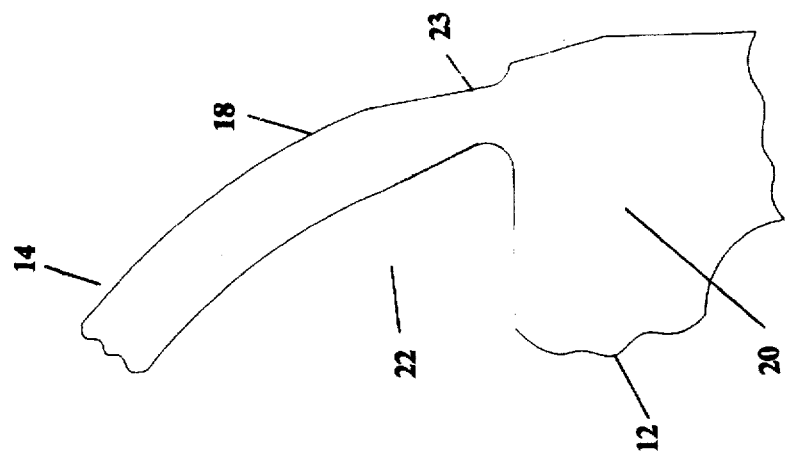
FIG. 5 is an exploded plan view of the hinge used with the present invention taken at circle 5 on FIG. 1.
Figure 4:
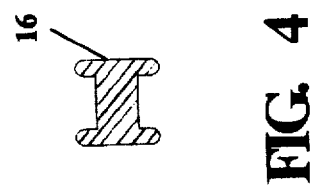
FIG. 4 is a cross-sectional view of the present invention taken along line 4—4 in FIG. 1.
Figure 3:
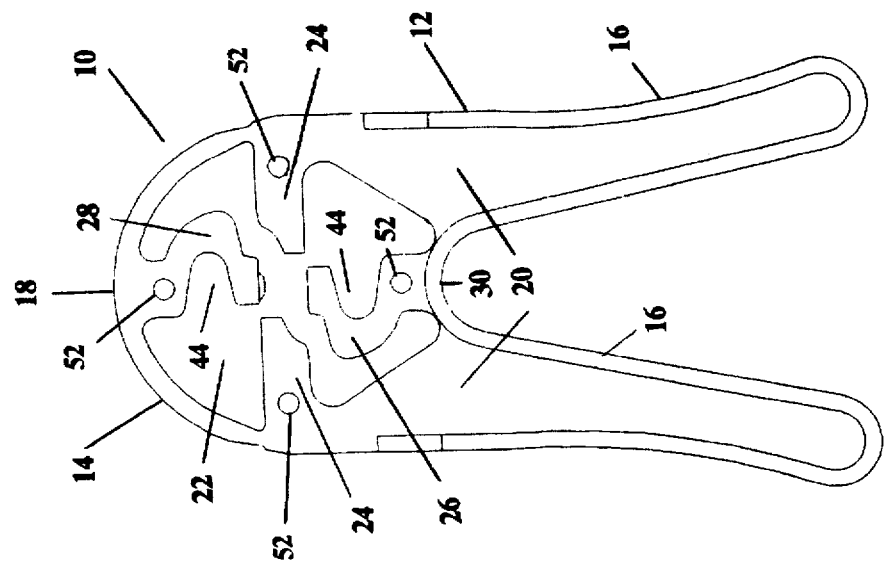
FIG. 3 is a bottom plan view of the intraocular lens folder of the present invention.
Figure 9:
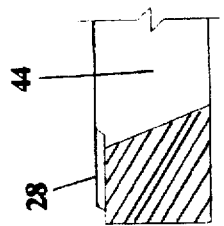
FIG. 9 is a cross-sectional view of the jaws of the present invention taken along line 9—9 in FIG. 6.
Figure 8:
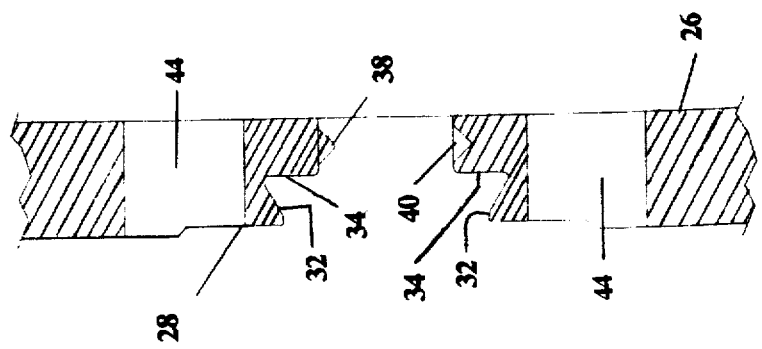
FIG. 8 is a cross-sectional view of the jaws of the present invention taken along line 8—8 in FIG. 6.
Figure 6:
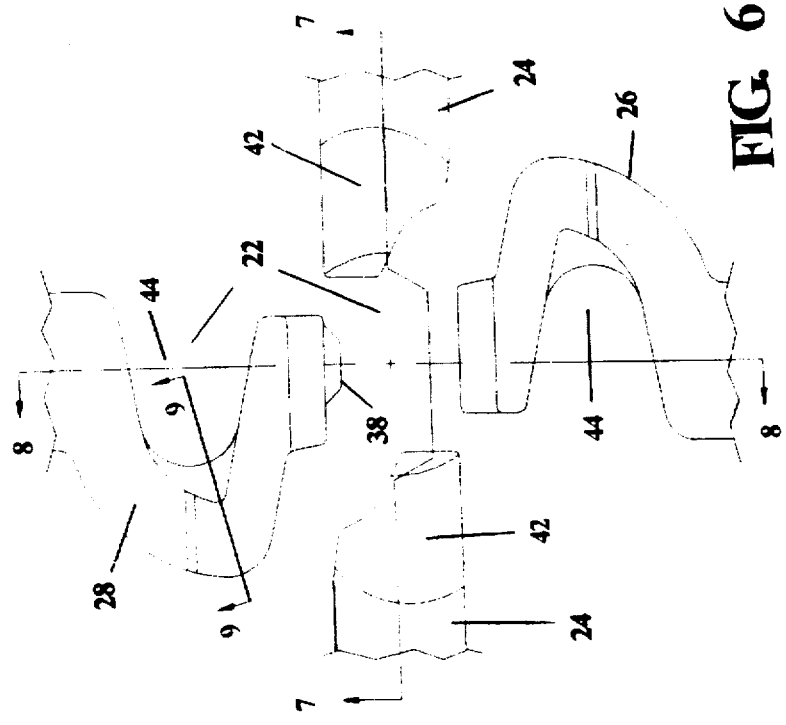
FIG. 6 is an exploded plan view of the jaws of the present invention.
Figure 7:
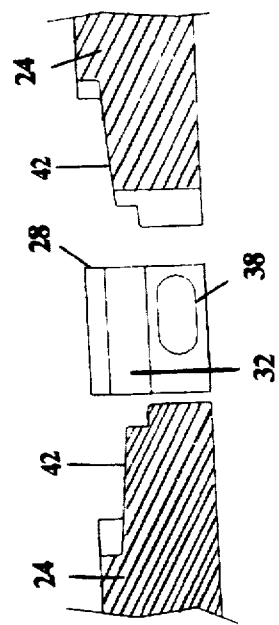
FIG. 7 is a cross-sectional view of the support jaws of the present invention taken along line 7—7 in FIG. 6.

As can best be seen in FIGS. 1, 2 and 3, upper portion 20 of handles 16 merge with rim 18 and hinges 23 to form head 14. Handles 16 are connected at hinge 30 and extend outwardly from hinge 30 at a sightly divergent angle. Handles 16 may be of any cross-sectional shape but an "T" cross-section, as shown in FIG. 4, is preferred.

In use, the IOL is placed within head 14 so that the IOL rests on sills 34 on jaw faces 32. The IOL is aligned along the desired folding axis either by placing the IOL in the preferred orientation or by rotating the IOL on sills 34 after initial IOL placement. The haptics may either rest within recesses 42 on support jaws 24 or above passages 44 in folding jaws 26 and 28. Force is applied to handles 16 so that handles 16 pivot toward each other about hinge 30. As handles 16 pivot toward each other about hinge 30, upper portions 20 of handles 16 are drawn away from each other. Pulling upper portions 20 of handles 16 away from each other causes jaws 24 to be pulled away from each other and also increases that radius of rim 18 at hinges 23 (see FIG. 5), thereby flattening out rim 18. As rim 18 is flattened, jaw 28 is forced toward jaw 26. The IOL, being captured between jaws 28 and 26 by relieved jaw faces 32, is forced to bend or fold longitudinally and outwardly or away from sills 34, thereby allowing the IOL to be removed easily from folder 10 in a folded configuration. When the haptics are aligned above passages 44, clearance is provided for the haptics to pivot downward, thereby allowing the IOL to be folded along a different axis.

Figure 11:
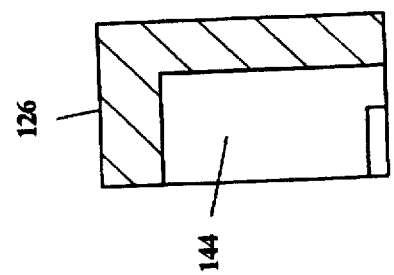
FIG. 11 is a cross-sectional view of the serpentine support jaw of the second embodiment of the present invention taken along line 11—11 in FIG. 10.
Figure 10:
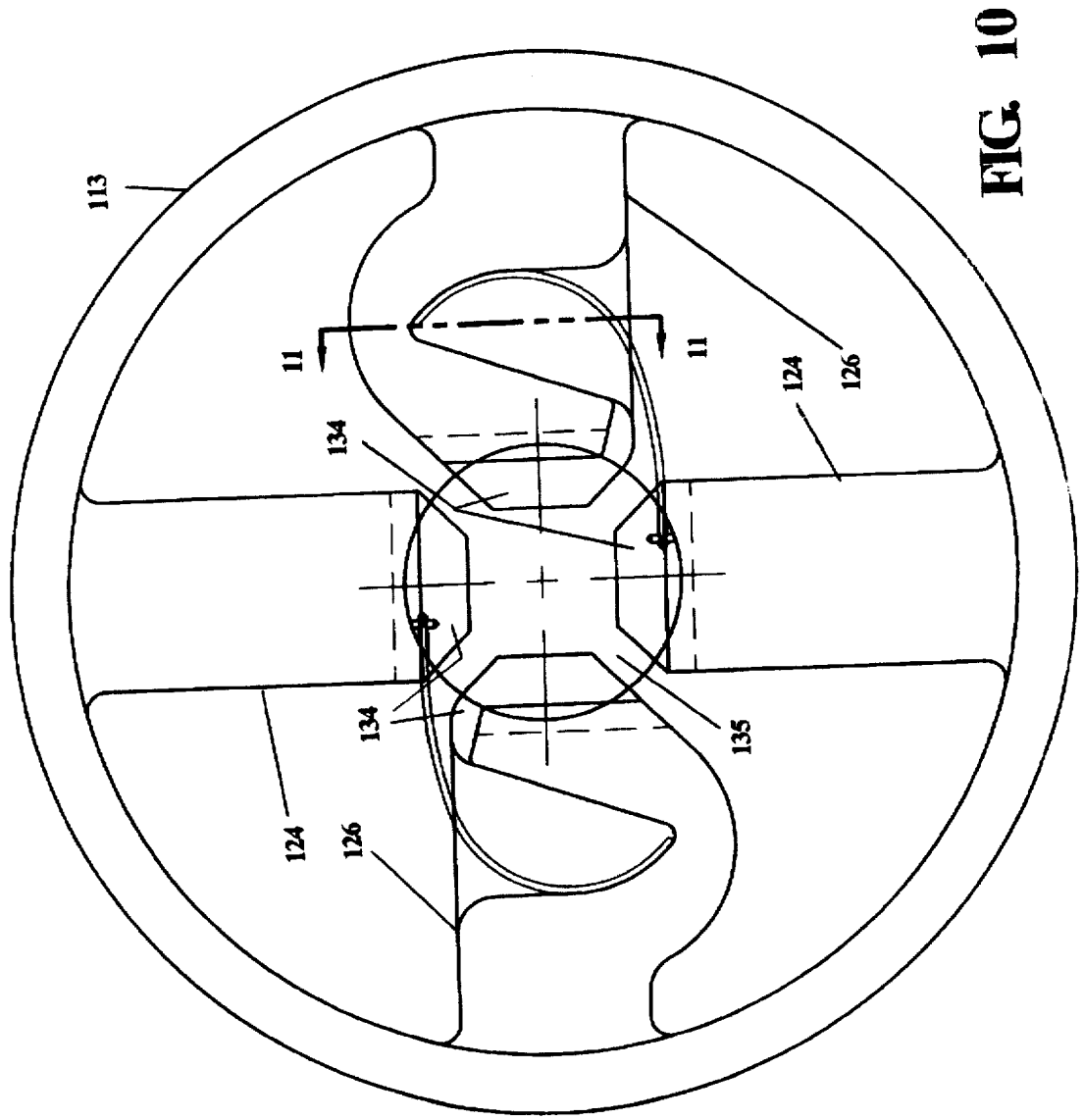
FIG. 10 is an exploded plan view of folding head of a second embodiment of the present invention.

In a second embodiment of the present invention, illustrated in FIGS. 10–16, folder 110 has frame 112 and removable carriage 113 that fits within head 114 of frame 112. Carriage 113 contains two sets of opposing jaws 124 and 126. As best seen in FIGS. 10, 11 and 16 jaws 124 and 126 contain clamping faces 132 that are undercut or relieved and contain a sill 134, thereby providing a stable platform for positioning the IOL 135 and ensuring that IOL 135 will consistently fold in the correct direction, as shown in FIG. 16. Jaws 126 are generally serpentine in shape and form passages 144, useful in the manner described above.

As best seen in FIGS. 12–15, in use, carriage 113 is rotated to align jaws 126 either horizontally (FIGS. 12 and 13) or vertically (FIGS. 14 and 15). Squeezing handles 116 will cause either jaws 124 (FIG. 13) or jaws 126 (FIG. 15) to be pressed together, thereby folding IOL 135.

This description is given for purposes of illustration and explanation. It will be apparent to those skilled in the relevant art that changes and modifications may be made to the invention described above without departing from its scope or spirit.

We claim:

1. An intraocular lens folder for allowing a lens' haptics pivot downward during folding, said intraocular lens folder comprising:

a) a first handle and a second handle, both handles having upper portions;

b) a hinge connecting the first handle to the second handle at the upper portions of the first and second handles;

c) a deformable rim generally arcuate in shape extending between the upper portion of the first handle and the upper portion of the second handle thereby defining a half ring-like head with a hollow center;

d) a first serpentine jaw located on the rim generally opposite the hinge and projecting into the hollow center; and e) a second serpentine jaw located at the hinge and projecting into the hollow center generally toward the first serpentine jaw.

2. The intraocular lens folder of claim 1 further comprising a third jaw and a fourth jaw, the third jaw and the fourth jaw having recesses and projecting into the hollow center from the upper portions of the first handle and the second handle, respectively.

3. The intraocular lens folder of claim 1 wherein the first serpentine jaw and the second serpentine jaw have jaw faces, the jaw face of the second serpentine jaw having a pin that fits into a hole on the jaw face of the first serpentine jaw.

4. The intraocular lens folder of claim 1 wherein the first serpentine jaw and the second serpentine jaw have jaw faces, the jaw face of the first serpentine jaw having a pin that fits into a hole on the jaw face of the second serpentine jaw.

5. An intraocular lens folder for allowing a lens' haptics pivot downward during folding, said intraocular lens folder comprising:

a) a first handle and a second handle, both handles having upper portions;

b) a hinge connecting the first handle to the second handle at the upper portions of the first and second handles;

c) a deformable rim generally arcuate in shape extending between the upper portion of the first handle and the upper portion of the second handle thereby defining a half ring-like head with a hollow center;

d) a first serpentine jaw located on the rim generally opposite the hinge and projecting into the hollow center;

e) a second serpentine jaw located at the hinge and projecting into the hollow center generally toward the first serpentine jaw;

f) a third jaw having a recess and projecting into the hollow center from the upper portion of the first handle; and g) a fourth jaw having a recess and projecting into the hollow center from the upper portion of the second handle.

6. The intraocular lens folder of claim 5 wherein the first serpentine jaw and the second serpentine jaw have jaw faces, the jaw face of the second serpentine jaw having a pin that fits into a hole on the jaw face of the first serpentine jaw.

7. The intraocular lens folder of claim 5 wherein the first serpentine jaw and the second serpentine jaw have jaw faces, the jaw face of the first serpentine jaw having a pin that fits into a hole on the jaw face of the second serpentine jaw.

8. An intraocular lens folder for allowing a lens' haptics pivot downward during folding, said intraocular lens folder comprising:

a) a first handle and a second handle, both handles having upper portions;

b) a hinge connecting the first handle to the second handle at the upper portions of the first and second handles;

c) a deformable rim generally arcuate in shape extending between the upper portion of the first handle and the upper portion of the second handle thereby defining a half ring-like head with a hollow center;

d) a carriage rotatably fixed within the hollow center of the head;

d) a first serpentine jaw located on the carriage; and e) a second serpentine jaw located on the carriage and projecting toward the first serpentine jaw.

* * * * *